(12) United States Patent
Inzer (10) Patent No.: US 9,895,594 B2
(45) Date of Patent: *Feb. 20, 2018

(54) WEIGHTLIFTING WRAP

(71) Applicant: Inzer Advance Designs, Inc., Longview, TX (US)

(72) Inventor: John Inzer, Longview, TX (US)

(73) Assignee: Inzer Advance Designs, Inc., Longview, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/581,162

(22) Filed: Apr. 28, 2017

(65) Prior Publication Data

US 2017/0225060 A1  Aug. 10, 2017

Related U.S. Application Data

(63) Continuation of application No. 14/639,267, filed on Mar. 5, 2015, now Pat. No. 9,731,160, which is a continuation of application No. 13/338,958, filed on Dec. 28, 2011, now Pat. No. 9,011,305.

(51) Int. Cl.
| | | |
|---|---|---|
| A63B 71/00 | (2006.01) | |
| A63B 71/12 | (2006.01) | |
| A63B 21/072 | (2006.01) | |
| A63B 23/04 | (2006.01) | |

(52) U.S. Cl.
CPC ...... *A63B 71/1225* (2013.01); *A63B 21/0724* (2013.01); *A63B 23/0405* (2013.01); *A63B 2023/0411* (2013.01); *A63B 2071/125* (2013.01); *A63B 2209/00* (2013.01)

(58) Field of Classification Search
USPC .......................................... 482/121–129, 148
See application file for complete search history.

(56) References Cited

U.S. PATENT DOCUMENTS

| | | |
|---|---|---|
| 2,285,335 A | 6/1942 | Hurt |
| 2,735,426 A | 2/1956 | Claydon |
| 2,811,154 A | 10/1957 | Scholl |
| 3,214,501 A | 10/1965 | Strauss |
| 3,409,008 A | 11/1968 | Mortensen et al. |
| 3,519,527 A | 7/1970 | Crowley |
| 3,711,868 A | 1/1973 | Kristof |
| 3,895,153 A | 7/1975 | Johnston et al. |
| 3,914,487 A | 10/1975 | Azoulay |
| 4,018,957 A | 4/1977 | Werner et al. |
| 4,137,356 A | 1/1979 | Shoemaker et al. |
| 4,236,550 A | 12/1980 | Braun et al. |
| 4,367,733 A | 1/1983 | Stromgren |
| 4,411,943 A | 10/1983 | Akao |
| 4,424,808 A | 1/1984 | Schaefer et al. |
| 4,552,713 A | 11/1985 | Cavicchioli |
| 4,699,133 A | 10/1987 | Schaefer et al. |

(Continued)

*Primary Examiner* — Stephen R Crow
(74) *Attorney, Agent, or Firm* — Dinsmore & Shohl, LLP (57) ABSTRACT

A weightlifting wrap is provided which prevents slippage, increases rebound potential, allows simpler application, and provides greater stability. The wrap includes a stretchable material having exposed elongate pliable strand members on one outer surface of the wrap. The exposed pliable strand members are arranged in an offset lattice configuration. The exposed pliable strand members may have a coefficient of friction sufficient to grip the previous layer of wrap.

13 Claims, 7 Drawing Sheets

(56) References Cited

U.S. PATENT DOCUMENTS

| | | | |
|---|---|---|---|
| 4,984,566 A * | 1/1991 | Sekine | A61F 13/00012 428/76 |
| 4,994,278 A | 2/1991 | Sablotsky et al. | |
| 5,407,421 A * | 4/1995 | Goldsmith | A61F 5/012 128/882 |
| 5,480,377 A | 1/1996 | Cartmell et al. | |
| 5,501,679 A * | 3/1996 | Krueger | B29C 55/023 428/152 |
| 5,691,034 A * | 11/1997 | Krueger | B29C 55/023 428/152 |
| 5,887,277 A * | 3/1999 | Lohman | A41D 13/08 2/16 |
| 5,948,707 A | 9/1999 | Crawley et al. | |
| 6,048,326 A * | 4/2000 | Davis | A61F 5/0106 602/26 |
| 6,194,629 B1 | 2/2001 | Bernhard | |
| 6,267,744 B1 | 7/2001 | Roberts et al. | |
| 6,402,712 B1 * | 6/2002 | Gauvry | A61F 13/062 602/26 |
| 6,449,988 B1 | 9/2002 | Roell | |
| 6,503,855 B1 | 1/2003 | Menzies et al. | |
| 6,811,540 B1 | 11/2004 | Ritchie | |
| 6,894,204 B2 | 5/2005 | Dunshee | |
| 7,048,708 B2 | 5/2006 | Evans et al. | |
| 7,311,685 B1 | 12/2007 | Policastro, Jr. | |
| 7,854,716 B2 | 12/2010 | Schuren et al. | |
| 7,886,776 B2 | 2/2011 | Jung et al. | |
| 7,937,852 B1 * | 5/2011 | Krehbiel | A41D 17/00 2/22 |
| 8,034,013 B2 | 10/2011 | Winkler | |
| 8,083,764 B2 | 12/2011 | Dedo | |
| 8,142,382 B2 | 3/2012 | Vito et al. | |
| 8,403,873 B2 | 3/2013 | Schuren et al. | |
| 8,556,841 B2 * | 10/2013 | Daneshvar | A61F 13/0273 602/41 |
| 8,641,653 B2 | 2/2014 | Winkler | |
| 8,950,016 B2 | 2/2015 | Depplito | |
| 9,011,305 B2 * | 4/2015 | Inzer | A63B 71/1225 482/148 |
| 9,062,231 B2 | 6/2015 | Wisnefsky et al. | |
| 9,415,256 B2 * | 8/2016 | Inzer | A63B 71/1225 |
| 2004/0098841 A1 * | 5/2004 | Crosby | B65D 63/10 24/16 R |
| 2005/0107725 A1 * | 5/2005 | Wild | A61H 9/0071 601/152 |
| 2007/0022519 A1 * | 2/2007 | South | A41B 11/02 2/239 |
| 2007/0131239 A1 | 6/2007 | Harrison et al. | |
| 2008/0156340 A1 | 7/2008 | Hopper et al. | |
| 2008/0280737 A1 | 11/2008 | Cook | |
| 2012/0059302 A9 * | 3/2012 | Hou | B32B 5/04 602/75 |
| 2012/0066809 A1 * | 3/2012 | Goth | A41D 13/088 2/16 |
| 2015/0174442 A1 | 6/2015 | Inzer | |

\* cited by examiner

WEIGHTLIFTING WRAP

CROSS-REFERENCE TO RELATED CASES

This application claims the benefit of U.S. patent application Ser. No. 14/639,267, filed Mar. 5, 2015, which is a continuation of U.S. patent application Ser. No. 13/338,958, filed Dec. 28, 2011, now U.S. Pat. No. 9,011,305.

BACKGROUND

Weightlifters wear supportive weightlifting wraps for two primary reasons: to protect and provide stability to the joints; and to provide kinetic energy during joint flexion (thereby increasing the amount of weight they can lift in exercises that require bending of the joints). Examples of exercises that require joint bending may include: squats; dead lifts; lunges; leg extensions; leg presses; dumbbell bench press; triceps kick backs; and bicep curls.

An example of the use of weightlifting wraps for support includes the use of weightlifting wraps around the knees. In weightlifting exercises requiring knee bending, the heavy weights used exert tremendous point load pressure on the knee joints. Knee wraps hold the knee joint in place. As the knee moves into flexion, the knee wraps are compressed, thereby storing potential energy. As the knee is extended, and the angle of knee flexion decreases, the wraps "rebound" and return the potential absorbed in compression into kinetic energy. The rebound provides an increase in the amount of weight the lifter can lift.

Weightlifting wraps are typically constructed from flexible or elastic material that rebounds from being stretched. The weightlifter puts the wraps on by stretching and rolling each wrap tightly around the joint. After the full length of the wrap is wrapped on the joint, the end of the wrap is tucked into one of the layers of wrapped material. The weightlifting wraps provide support to athletes' joints. However, several problems exist concerning safety, effectiveness, and ease of use.

One problem of weightlifting wraps exists due to slippage of the individual layers of wrapped material. Each revolution of wrap lies down against wrap material of the revolution before it. A lack of friction between each layer causes the wrap to from the other layers during joint flexion. The slippage limits the amount of support the weightlifting wrap can provide the lifter. Sudden or intermittent slippage can cause loss of stability and cause injury to the weightlifter.

Weightlifters have attempted to address the problem of slippage by applying either "gym chalk" (magnesium carbonate) or "sticky-spray" (sticky solution in aerosol spray cans). The gym chalk or sticky spray helps the wrap layers to hold, or grip, to each other. Gym chalk may leave residue on the floor and clothing. In addition, gym chalk only provides a small amount of friction between the layers but does not stop the slipping. Sticky spray is difficult to clean off the skin and wrap material, toxic to breathe, attracts dirt, and rubs off on clothing. Both gym chalk and sticky spray are expensive, clutters a weightlifter's gym bag, and occupies space. Gym chalk and sticky spray require time to buy, apply, store, and organize.

Another problem presented by weightlifting wraps concerns limited rebound potential. Conventional weightlifting wraps are constructed of a yarn or cloth material and may sometimes include an elastic material on the inside of such wrap. In the example involving knee wraps, the yarn or cloth material making direct contact with the back of the knee provides inferior rebound, compared to the effects of having a rubber tennis ball behind the knee, for example. To get similar rebound from the use of yarn or cloth material would require densely wound wraps. Wrapping such wraps in a densely wound configuration presents several problems including: the requirement of a "modulus" (power required to pull the wrap tight) greater than a single lifter could pull with the arms; would squeeze the joints so severely that it would be too painful to keep the wrap on the joints; and would dramatically reduce circulation.

Another problem presented by such weightlifting wraps includes the difficulty of application. It is desirable to wrap the weightlifting wraps tightly to increase support, protection, and performance. During the wrapping of the joints, the hands of the lifter or the lifter's handler can lose grip on the wraps. Such knee wraps uncoil almost completely unless the wraps are kept in control by the hands or by tucking the end of the wraps inside a layer of wrap. The wrapping process must then be repeated. This repetitive process results in lost time, and lost mental and physical energy. Competitive lifters are given a certain amount of time (usually one to three minutes) to get on the platform and perform the exercise after the lifter's name is called. When a wrap uncoils before or during this time, the lifter faces a dilemma: lifting with an uncoiled wrap; or risking disqualification by attempting to re-wrap in time.

Another problem arises due to the instability of weightlifting wraps. Such weightlifting wraps may shift position during an exercise. This shift in position causes instability in the weightlifter and "jitteriness." This causes the lifter's muscles to work hard to compensate for the "jittery" motion. The extra work of the muscles reduces the lifter's overall performance and decreases the amount of weight the lifter can lift. This extra muscle work also requires more mental and physical energy output, resulting in loss of endurance during a tournament or workout. The instability also significantly reduces the protective benefit from weightlifting wraps. Therefore, a need arises for weightlifting wraps which prevent slippage, increase rebound potential, allow simpler application, and provide greater stability.

SUMMARY

Embodiments of the current invention are directed towards solving the need for weightlifting wraps which prevent slippage, increase rebound potential, allow simpler application, and provide greater stability. An embodiment of the invention comprises: a weightlifting wrap made of stretchable material; the wrap having exposed elongate pliable strand members on one outer surface of the wrap; and the exposed strand members are arranged in an offset lattice configuration. In some embodiments, the exposed strand members have a coefficient of friction sufficient to grip the previous layer of the wrap.

It is an object of one or more embodiments of the present invention to provide a weightlifting wrap which prevents sliding and slipping of the individual layers of the wrap.

It is another object of one or more embodiments of the present invention to provide a weightlifting wrap which provides rebound through the use of exposed elongate pliable strand members on one or both of the outer surfaces of the weightlifting wrap.

It is another object of one or more embodiments of the present invention to provide a weightlifting wrap which allows ease of application and incorporates exposed elongate pliable strand members on one or both of the outer surfaces of the weightlifting wrap to decrease the modulus during application.

It is another object of one or more embodiments of the present invention to provide a weightlifting wrap that incorporates exposed elongate pliable strand members on one or both of the outer surfaces of the weightlifting wrap which are woven into the fabric, and may be configured in an offset lattice configuration.

It is further an object of one or more embodiments of the present invention to provide a weightlifting wrap that incorporates exposed elongate pliable strand members on one or both of the outer surfaces of the weightlifting wrap, wherein the exposed strand members have a coefficient of friction sufficient to grip the previous layer of the wrap.

BRIEF DESCRIPTION OF THE DRAWINGS

These and other features, aspects and advantages of one or more embodiments of the present invention will become better understood with regard to the following description, appended claims, and accompanying drawings where:

DETAILED DESCRIPTION

Overview

In one embodiment, the weightlifting wrap integrates exposed elongate pliable strand members on at least one of the outer peripheral surface of the wrap. In this embodiment, the elongate pliable strand members comprise a natural or synthetic rubber and secure the material of the proximate layers of wrap, thereby fixedly engaging the layers wrap in place relative to the previous layer of wrap. This holding or gripping action prevents the wrap from sliding and slipping on itself. The weightlifter no longer needs to spray sticky or apply chalk to the wrap material. The weightlifter no longer has to breathe toxic fumes from sticky spray or dust from chalk. Clothing is kept clean of chalk and sticky spray. This saves time, laundry expense and wear-and-tear to clothing, gym bags and other gear that touch the wraps. The athlete saves time by simply picking up the wraps, rolling the wraps on the joints, and enjoying the benefits of secure joint protection and increased performance.

The exposed elongate pliable strand members of the weightlifting wrap of embodiments of the present invention provide a bulk of pliable material behind the joint of a wearer. The bulk of pliable material, such as rubber, behind the joint provides a superior rebound effect (as opposed to weightlifting wraps without exposed strands). The pliable strand members are compressed behind the joint during joint flexion. The compressed strand members react against the surfaces surrounding the joint and rebound the leg to a straight position with more kinetic energy return than weightlifting wraps without exposed strands.

In embodiments of the present invention, exposed elongate pliable strand members of the weightlifting wrap are integrated into the woven wrap material in a manner to maximize the coefficient of friction between the proximate wound layer; to provide elastic rebound; and to allow greater circulation due to the stretching of the pliable strand members. Rubber wrap designs which are not exposed (including rubber strands include inside a wrap, as opposed to outside of the wrap) must arranged be in a straight line. These straight-line rubber strands squeeze when stretched around the knee. Conversely, in embodiments of the current invention, a grouping of pliable strand members in the exposed strands of the weightlifting wrap can be relatively loosely wrapped. Accordingly, such a configuration does not increase the modulus and squeezing sensation of the wrap when tightly wound.

The maximum length a weightlifting wrap can be pulled is usually determined by the weave of the cloth yarn. In embodiments of the present invention, the looped or braided construction/arrangement of the exposed pliable strands is still relatively loose as the wraps reach maximum pulled length. This results in less squeezing on body tissues as well as providing more bulk behind the knees than stretched-out rubber or wadded cloth yarn.

Occasionally when wrapping, the weightlifter or the weightlifter's handler loses hand grip on the wrap. When slipping begins to occur, the weightlifting wrap of embodiments of the present invention do not uncoil, but merely lose tightness on only one revolution of wrap. The previously wrapped layers of the weightlifting wrap remain as tight as when they were first pulled tightly on the knees. The weightlifter or the weightlifter's handler simply starts wrapping where they left off. If the weightlifting wrap does become untucked, the wrap does not uncoil very far, usually less than two revolutions.

The weightlifting wrap of embodiments of the present invention reduce the "jittery" motion around the joints. As point load pressures are exerted on the joint, the weightlifting wrap of embodiments of the present invention stay tightly wrapped. Accordingly, the weightlifter conserves mental and physical energy which increases performance during competitions and workouts. Longevity and health are promoted due to the increased stability.

Specific Embodiments and Examples

An example of an embodiment of the invention is set forth in Drawing FIGS. 1-7, and is further described as the preferred design and best mode of carrying out the invention. According to the embodiment, the wrap comprises: weightlifting wraps 31 constructed of a pliable and stretchable material. The weightlifting wraps 31 have exposed strands of elongate pliable material 32 on at least one outer surface 33 of the weightlifting wrap. The exposed strands 32 arranged in an offset lattice configuration. In one or more embodiments, the exposed strands 32 are comprised of a natural or synthetic rubber and have a coefficient of friction sufficient to grip the previous layer of wrap.

The weightlifting wrap 31 of the one embodiment is constructed of stretchable cloth material. The weightlifting wrap 31 may be of varying length and width. However, in one embodiment, the weightlifting wrap 31 is two meters (2 m) long and three inches (3") wide. In one embodiment, the weightlifting wrap is constructed of 100% polyester. The weightlifting wrap in one embodiment have an approximate thickness of one-eighth of an inch (⅛").

The exposed elongate pliable strand members 32 are located on the outer surface 33 of the weightlifting wrap 31. The exposed strand members 32 ingress and egress the outer surface of the weightlifting wrap 31 in an offset lattice configuration as shown in Drawing FIG. 3. For purposes of this invention, the offset lattice configuration involves including a small length of an elongate pliable material such as synthetic rubber interwoven through the outer surface 33 of the weightlifting wrap 31. An individual elongate pliable member of the exposed strand 32 ingresses into the outer fabric of the weightlifting wrap 31 and extends a distance below the surface. The individual elongate pliable member of the exposed strand 32 egresses around the proximate elongate pliable member of the exposed strand 32, as shown in FIGS. 3-7. A plurality of small loops are wound in this way, and longitudinally extend the length of the weightlifting wrap 31. Additional rows of rubber loops are added adjacent to the previous row, and the point at which the exposed strand 32 enters the fabric is offset, in respect to the adjacent row, as shown and illustrated in Drawing FIGS. 3-7. A number of rows of exposed strands 32 adjacent to each other form a band 34 of exposed strand members. One embodiment of the weightlifting wrap includes two bands 34, wherein each band 34 is comprised of fourteen (14) rows of exposed pliable strand members, wherein each row extend longitudinally the length of the weightlifting wrap 31, as shown in Drawing FIGS. 3-7.

In one embodiment, the weightlifting wrap 31 is wrapped in such a manner that the exposed pliable strand members 32 face away from the skin. The weightlifting wrap 31 is wrapped tightly around the joint, with the exposed pliable strand members making contact with the next layer. During application and flexion of the joint, the weightlifting wrap 31 may stretch. The offset lattice configuration of the exposed pliable strands 32 allows the stretching to take place, without restricting blood flow. The compression of the exposed pliable strands 32 allows rebound on joint extension.

Alternatives

Figure 1:
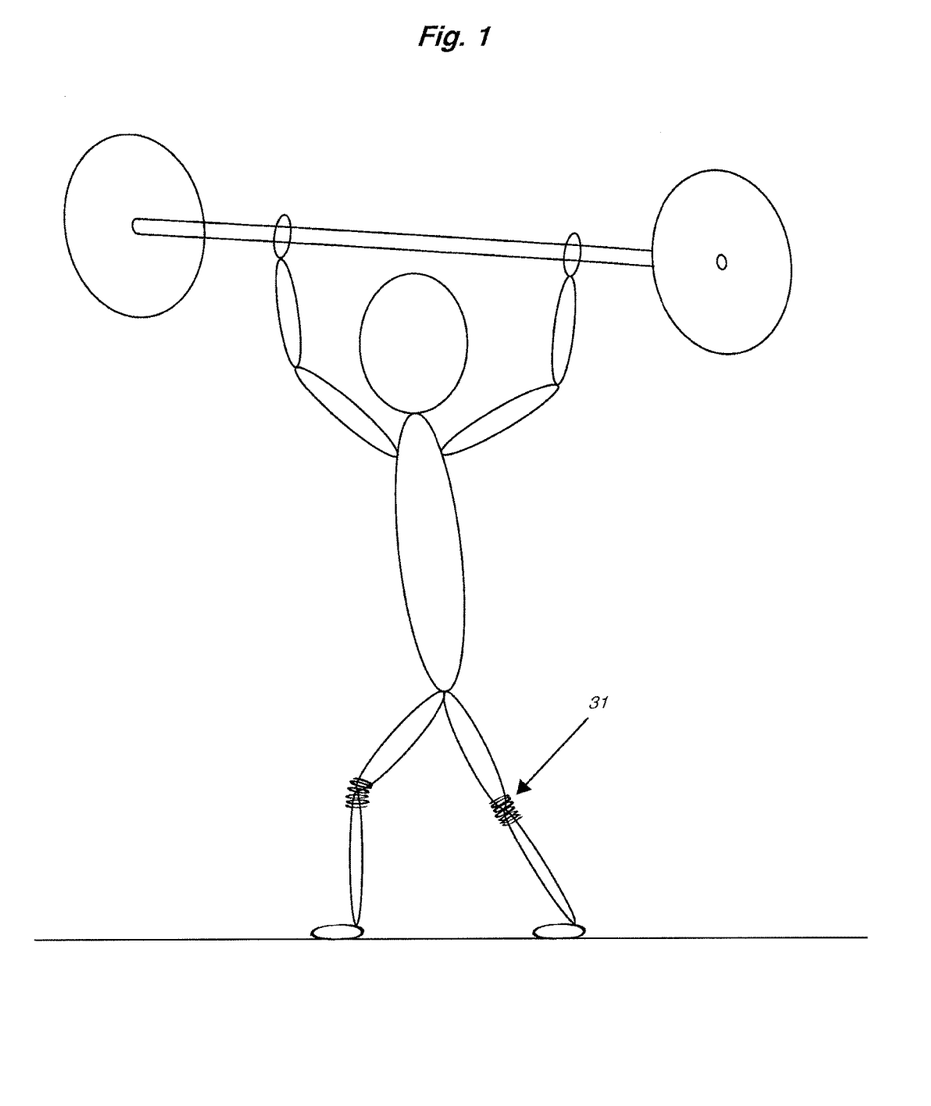
FIG. 1 shows a perspective illustration of a weightlifter engaging in a squatting exercise, showing an embodiment of weightlifting wraps wound around the knees.
Figure 2:
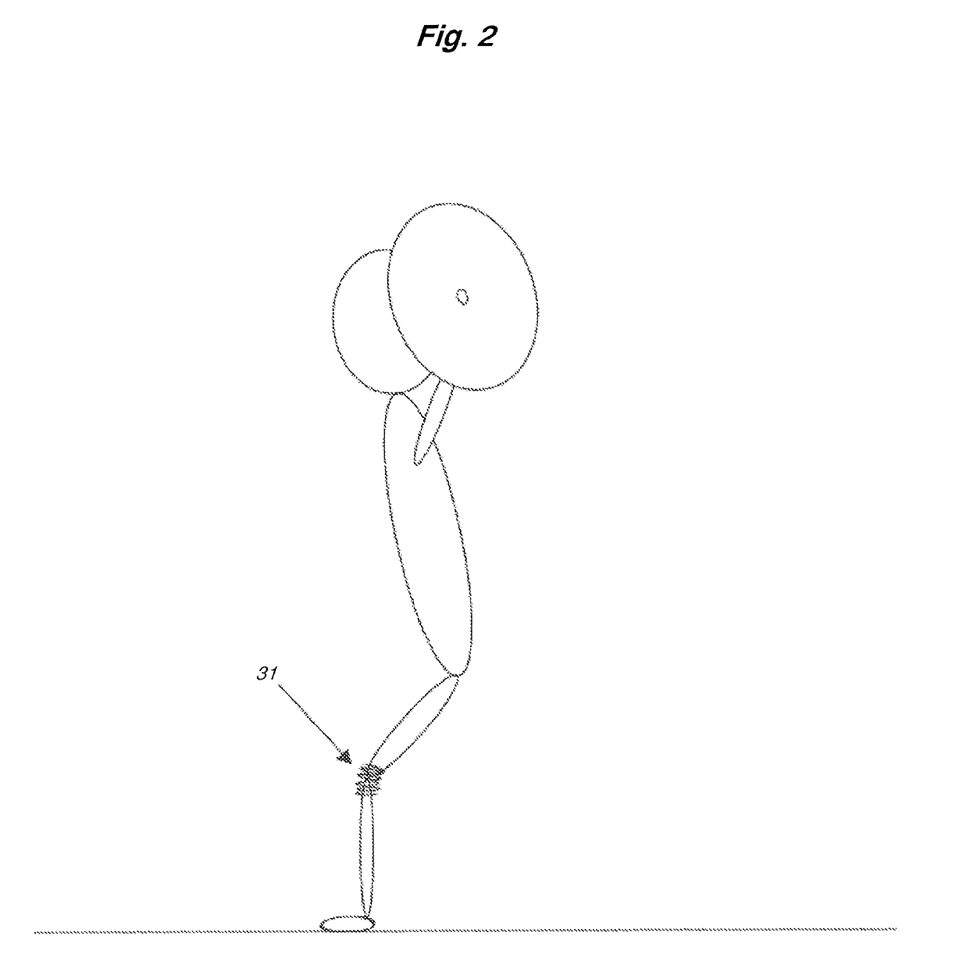
FIG. 2 shows a side view illustration of a weightlifter engaging in a squatting exercise, showing an embodiment of weightlifting wraps wound around the knees.
Figure 3:
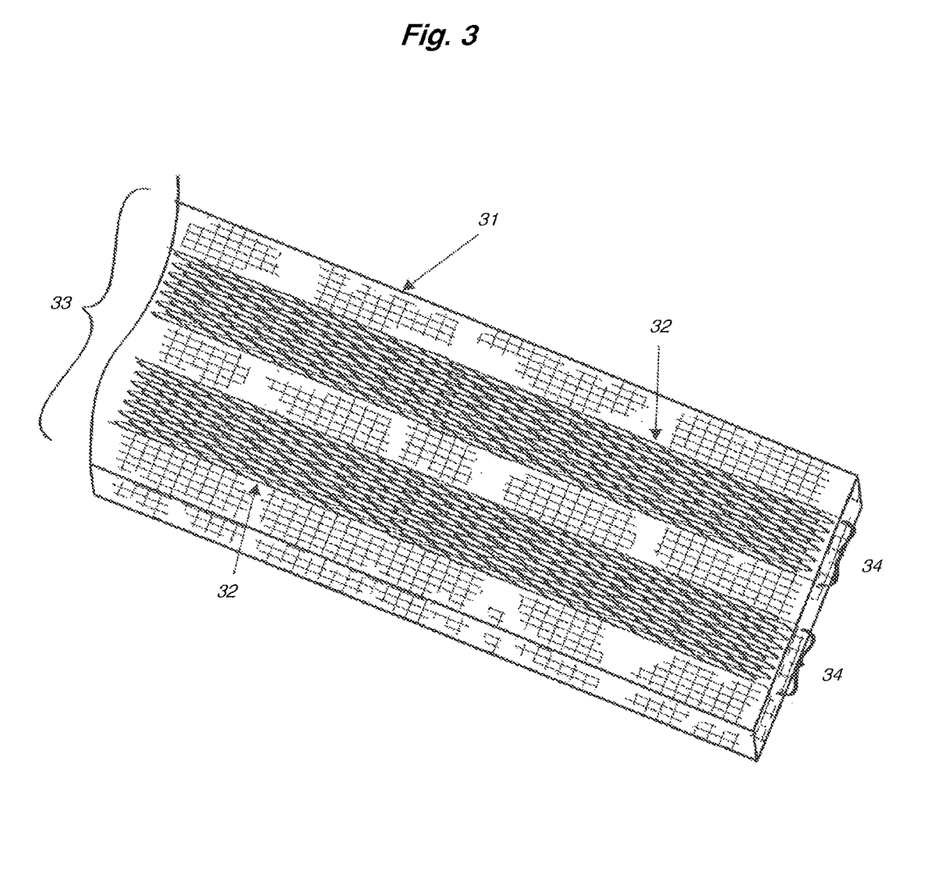
FIG. 3 shows a perspective view of an embodiment of the invention.
Figure 4:
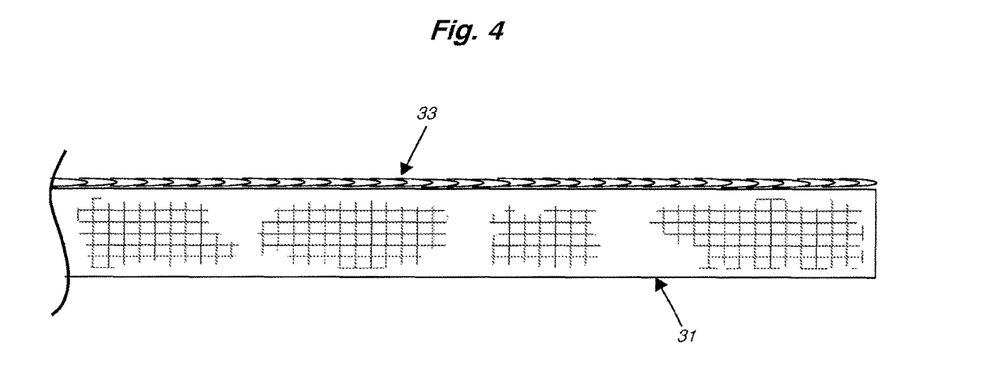
FIG. 4 shows a side view of the embodiment of FIG. 3.
Figure 5:
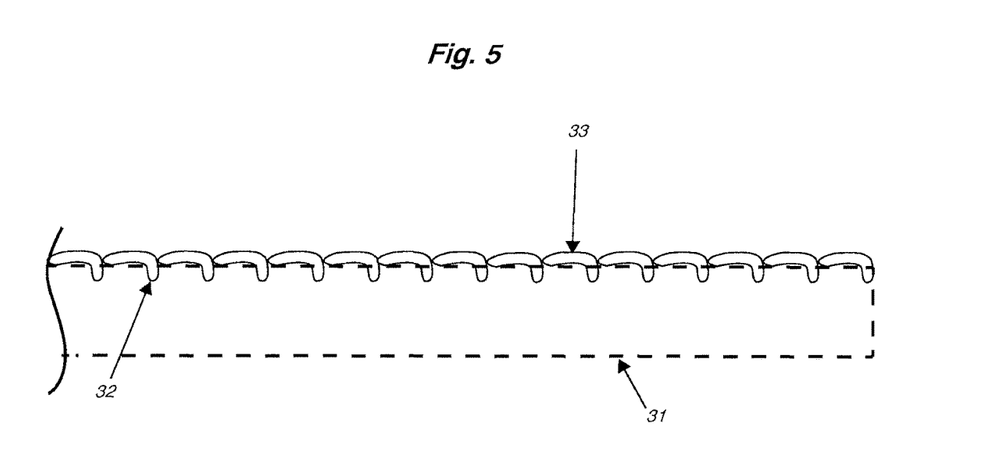
FIG. 5 shows a side sectional view of the embodiment of FIG. 3.
Figure 6:
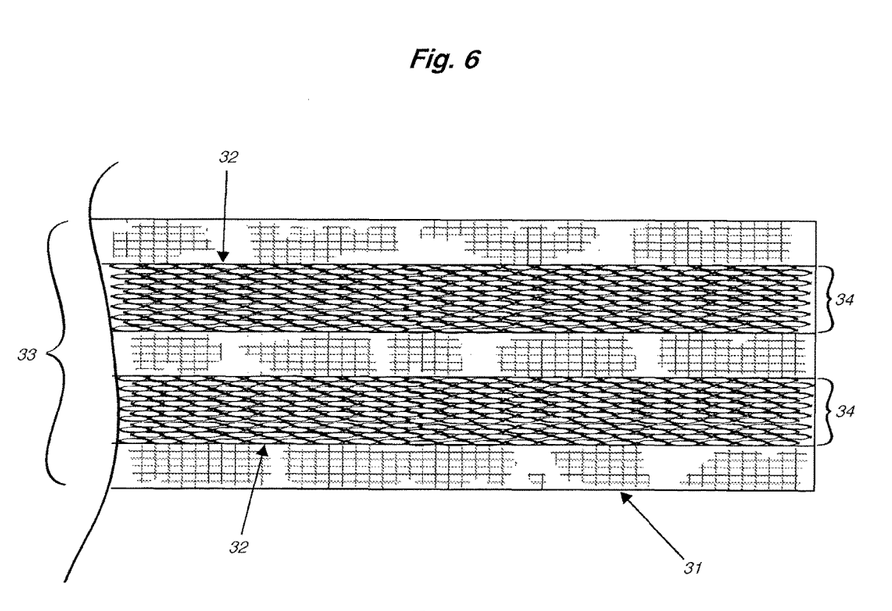
FIG. 6 shows a top view of the embodiment of FIG. 3.
Figure 7:
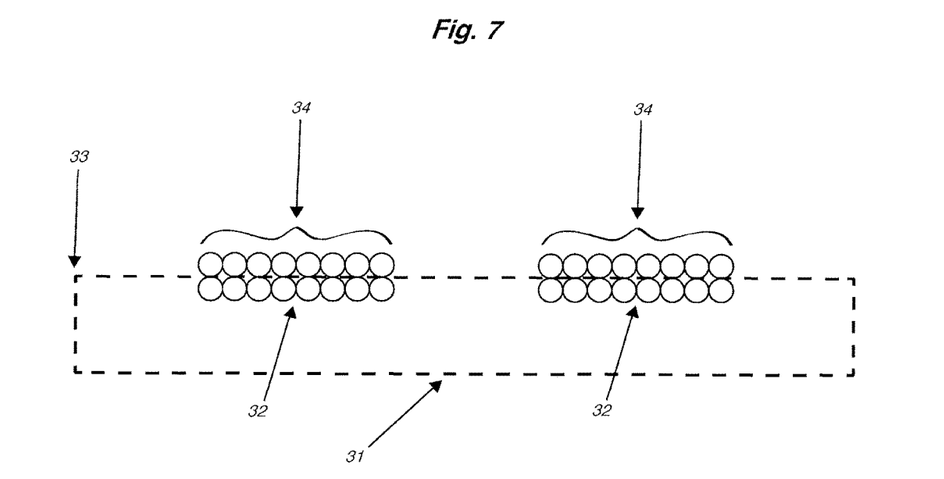
FIG. 7 shows a front sectional view of the embodiment of FIG. 3.
Figure 8:
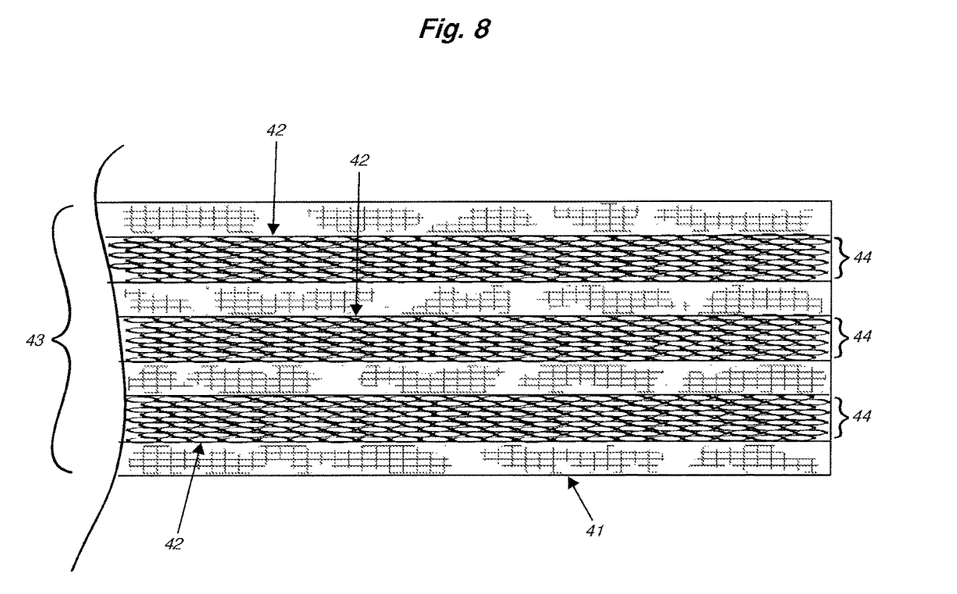
FIG. 8 shows a top view of an alternate embodiment of the invention, wherein the wrap has three bands of exposed elongate pliable strand members traversing longitudinally across the outer surface.

Differing configurations and designs are contemplated by embodiments of the present invention. For example, in an alternate embodiment, the structures and relational similarities of other embodiments are employed. However, in the embodiment, the weightlifting wrap 41, has three bands 44 of exposed pliable strand members 42 traversing longitudinally across the outer surface 43 distance of the weightlifting wrap 41. An example of this embodiment is illustrated in Drawing FIG. 8.

Figure 9:
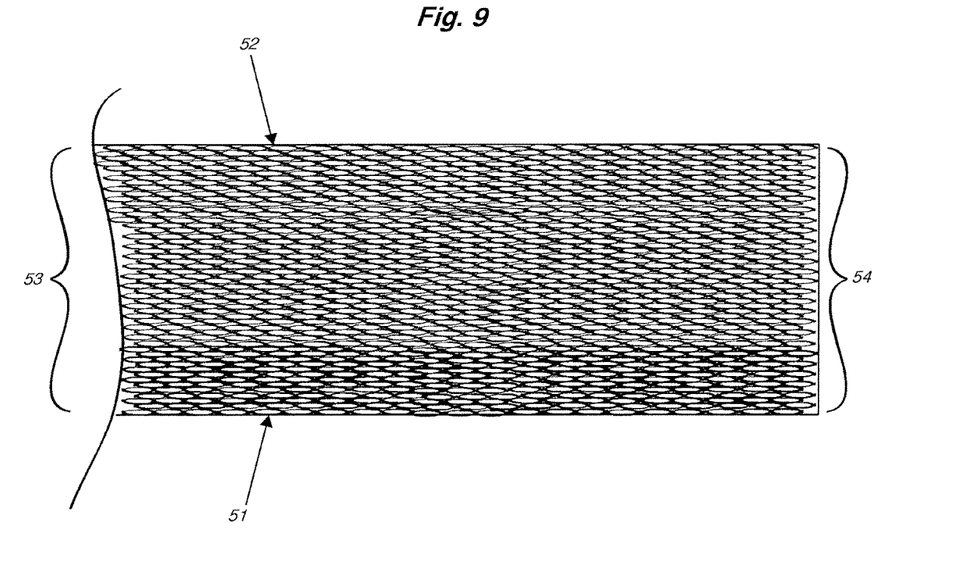
FIG. 9 shows a top view of an alternate embodiment of the invention, wherein the weightlifting wrap has one band of exposed elongate pliable strand members which cover the entire outer surface and traverse longitudinally the distance of the outer surface.

In another embodiment, the structures and relational similarities of other embodiments are employed. However, the weightlifting wrap 51 has one band 54 of exposed pliable strand members 52 which covers the entire outer surface 53, and traverses longitudinally the distance of the weightlifting wrap 51. An example of this embodiment is illustrated in Drawing FIG. 9.

Figure 10:
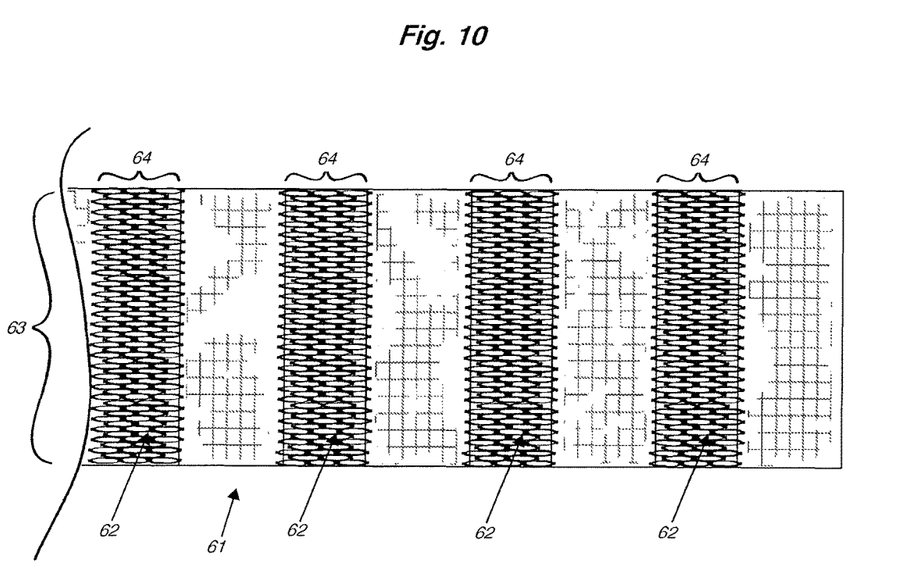
FIG. 10 shows a top view of an alternate embodiment of the invention, wherein the weightlifting wraps have a plurality of bands of exposed elongate pliable strand members which extend longitudinally perpendicular across the outer surface.

In another embodiment, the structures and relational similarities of other embodiments are employed. The weightlifting wrap 61 has a plurality of bands 64 of exposed pliable strand members 62 which extend longitudinally perpendicular across the outer surface 63, as illustrated in Drawing FIG. 10. The plurality of bands 64 extend the distance of the weightlifting wrap 61. An example of this embodiment is illustrated in Drawing FIG. 9.

In other embodiments, the materials used may differ. For example, the weightlifting wrap 31 may be constructed from: polyester; elastic; cotton fiber, medical crepe; or combinations and equivalents thereof. The loft of yarn used may vary. In one embodiment, the loft of yarn was chosen such that the weightlifting wraps were tightly woven and presented a softer surface to the underlying tissue. Alternatively, a loft of yarn may be used that presents a harder surface to the underlying tissue.

In other embodiments, the configuration, placement, length, width, and placement of bands 34 may differ according to alternate embodiments. For example, the exposed pliable strand members 32 can be arranged so that they encompass differing patterns, and shapes, and encompass differing dimensional relationships. The width, length, and thickness of the weightlifting wrap 31 may also differ. In other embodiments, the exposed pliable strand members may be interwoven through both outer sides of the weightlifting wrap in the configurations previously set forth. The exposed pliable strand members 32 may also be constructed of a different material such as rubber to have a coefficient of friction great enough to grip the previous layer of the wrap.

Use of embodiments of the current invention may applied in weightlifting exercises or in situations where it is desirable for an athlete or weightlifter to provide support and kinetic energy rebound to the joints. Examples of embodiments of the present invention as previously set forth were directed towards knee wraps. However it is also contemplated that the wrap may be used on other parts of the body. For example, the weightlifting wrap may be placed on the: ankles, legs, knees, waist, torso, elbows, or wrists.

Differing combinations and permutations of the embodiments set forth are contemplated by the present invention. Additionally, all functional equivalents of materials used and means of attachment of elements are contemplated by the present invention. Therefore, the spirit and scope of the appended claims should not be limited to the descriptions of the preferred versions and alternate embodiments set forth herein.

Any element in a claim that does not explicitly state "means for" performing a specified function, or "step for" performing a specific function, is not to be interpreted as a "means" or "step" clause as specified in 35 USC §112(f). In particular, the use of "step of" in the claims herein is not intended to invoke the provisions of 35 USC §112(f).

What is claimed is:

1. A weightlifting wrap constructed of a stretchable woven material, said weightlifting wrap including a plurality of exposed elongate pliable strand members on at least one outer surface of said weightlifting wrap, said plurality of elongate pliable strand members being arranged into at least two separate bands on at least one of said outer surfaces of said weightlifting wrap, each of said bands comprising a plurality of adjacent rows of said elongate pliable strand members.

2. A weightlifting wrap as claimed in claim 1, wherein each of said bands comprises 14 adjacent rows of elongate pliable strand members.

3. A weightlifting wrap as claimed in claim 2, wherein said adjacent rows of said elongate pliable strand members in each band ingress and egress said at least one outer surface of said weightlifting wrap in an offset lattice configuration.

4. A weightlifting wrap as claimed in claim 1, wherein said elongate pliable stand members comprise rubber strands.

5. A weightlifting wrap as claimed in claim 4, wherein said rubber stands comprise synthetic rubber strands.

6. A weightlifting wrap as claimed in claim 1, wherein said stretchable woven material comprises at least one of polyester or cotton fiber.

7. A weightlifting wrap as claimed in claim 1, wherein said weightlifting wrap has a length and a width and each row of said plurality of adjacent rows of said elongate pliable stand members extends longitudinally the length of said wrap.

8. A weightlifting wrap as claimed in claim 7, wherein said length of said weightlifting wrap is 2 meters.

9. A weightlifting wrap as claimed in claim 7, wherein said width of said weightlifting wrap is 3 inches.

10. A weightlifting wrap constructed of a stretchable woven material, said weightlifting wrap having a plurality of exposed rubber strands on at least one outer surface of said weightlifting wrap, said plurality of rubber strands being arranged into separate bands on at least one of said outer surfaces of said weightlifting wrap, each of said bands comprising a plurality of rows of said rubber strands, and wherein when said weightlifting wrap is wrapped in successive layers around a joint of a user, said exposed rubber strands have a coefficient of friction sufficient to grip proximate layers of said weightlifting wrap.

11. A weightlifting wrap as claimed in claim 10, wherein said rows of rubber strands extend longitudinally substantially the length of said weightlifting wrap.

12. A weightlifting wrap as claimed in claim 10, wherein said rows of rubber strands extend substantially across the width of said weightlifting wrap.

13. A weightlifting wrap as claimed in claim 12 in which said rubber strands extend substantially perpendicular to the lengthwise direction of said weightlifting wrap.

\* \* \* \* \*

UNITED STATES PATENT AND TRADEMARK OFFICE
CERTIFICATE OF CORRECTION

PATENT NO. : 9,895,594 B2
APPLICATION NO. : 15/581162
DATED : February 20, 2018
INVENTOR(S) : John Inzer Page 1 of 2

It is certified that error appears in the above-identified patent and that said Letters Patent is hereby corrected as shown below:

In the Specification

Column 1, Line 44:
"the wrap to from the other layers during joint flexion. The"
Should read:
--the wrap to form the other layers during joint flexion. The--; and Column 4, Line 22:
"of the wrap) must arranged be in a straight line. These"
Should read:
--of the wrap) must be arranged in a straight line. These--; and Column 5, Line 11:
"weightlifting wrap in one embodiment have an approximate"
Should read:
--weightlifting wrap in one embodiment has an approximate--; and Column 6, Line 34:
"Use of embodiments of the current invention may applied"
Should read:
--Use of embodiments of the current invention may be applied--; and In the Claims Column 7, Line 10, Claim 4:
"said elongate pliable stand members comprise rubber"
Should read:
--said elongate pliable strand members comprise rubber--; and Signed and Sealed this
First Day of January, 2019

Andrei Iancu
*Director of the United States Patent and Trademark Office*

CERTIFICATE OF CORRECTION (continued)
U.S. Pat. No. 9,895,594 B2

Column 7, Line 20, Claim 7:
"pliable stand members extends longitudinally the length of"
Should read:
--pliable strand members extends longitudinally the length of--.